United States Patent [19]

Dunn

[11] 4,282,481
[45] Aug. 4, 1981

[54] APPARATUS FOR MEASURING THE LOCAL VOID FRACTION IN A FLOWING LIQUID CONTAINING A GAS

[75] Inventor: Patrick F. Dunn, Downers Grove, Ill.

[73] Assignee: The United States of America as represented by the United States Department of Energy, Washington, D.C.

[21] Appl. No.: 58,339

[22] Filed: Jul. 17, 1979

[51] Int. Cl.³ ............................................ G01R 27/02
[52] U.S. Cl. ............................... 324/65 P; 324/65 R; 324/446
[58] Field of Search .................. 324/65 R, 65 P, 439, 324/446, 447

[56] References Cited
U.S. PATENT DOCUMENTS 3,271,671  9/1966  Coulter .............................. 324/439

OTHER PUBLICATIONS

Hewitt et al., EPRI NP-118, Final Report "Experimental Methods . . .", Mar. 1976, pp. 70 plus.

Primary Examiner—Ernest F. Karlsen
Attorney, Agent, or Firm—Donald P. Reynolds; Frank H. Jackson; James E. Denny

[57] ABSTRACT

The local void fraction in liquid containing a gas is measured by placing an impedance-variation probe in the liquid, applying a controlled voltage or current to the probe, and measuring the probe current or voltage. A circuit for applying the one electrical parameter and measuring the other includes a feedback amplifier that minimizes the effect of probe capacitance and a digitizer to provide a clean signal. Time integration of the signal provides a measure of the void fraction, and an oscilloscope display also shows bubble size and distribution.

10 Claims, 7 Drawing Figures

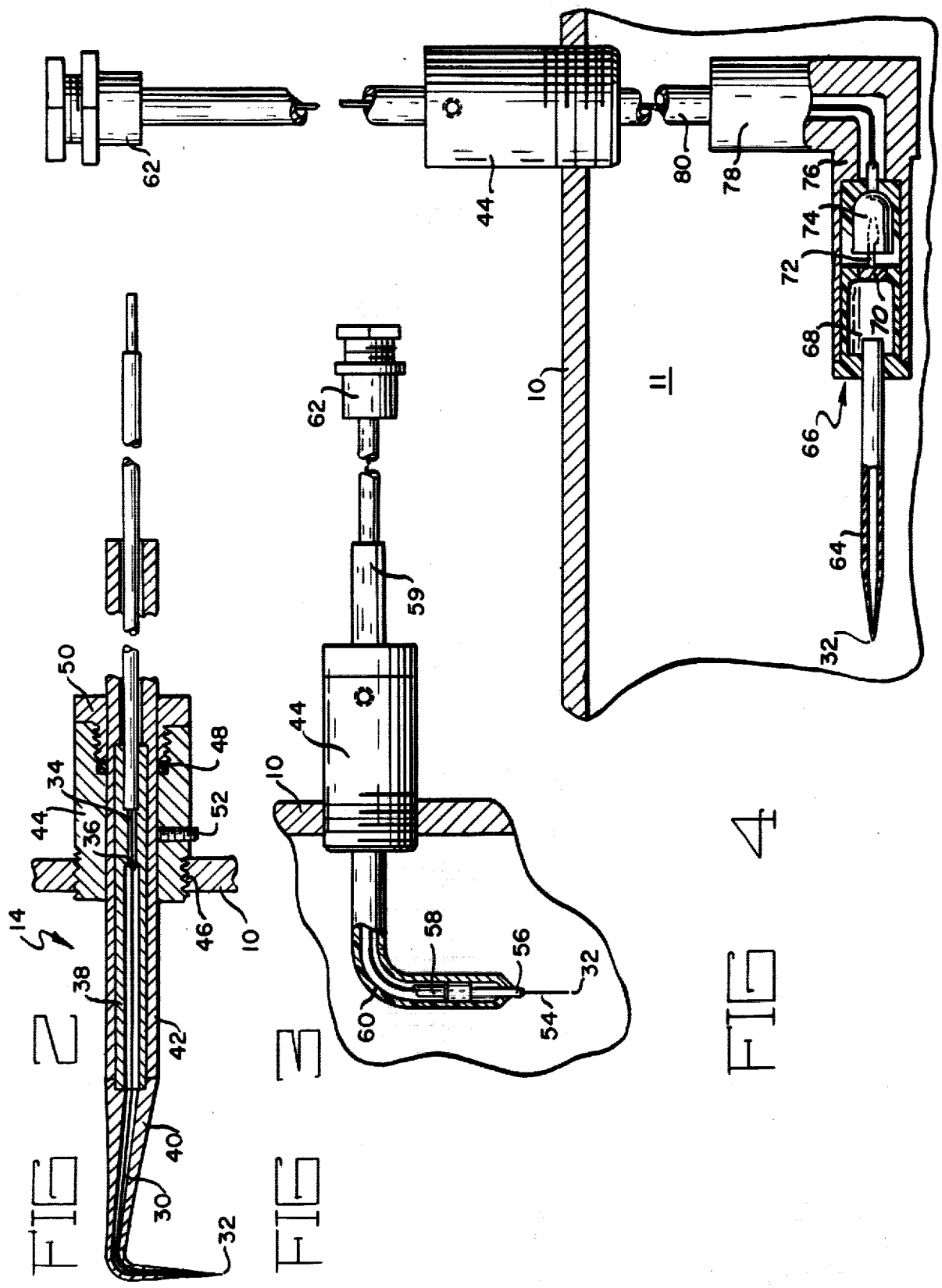

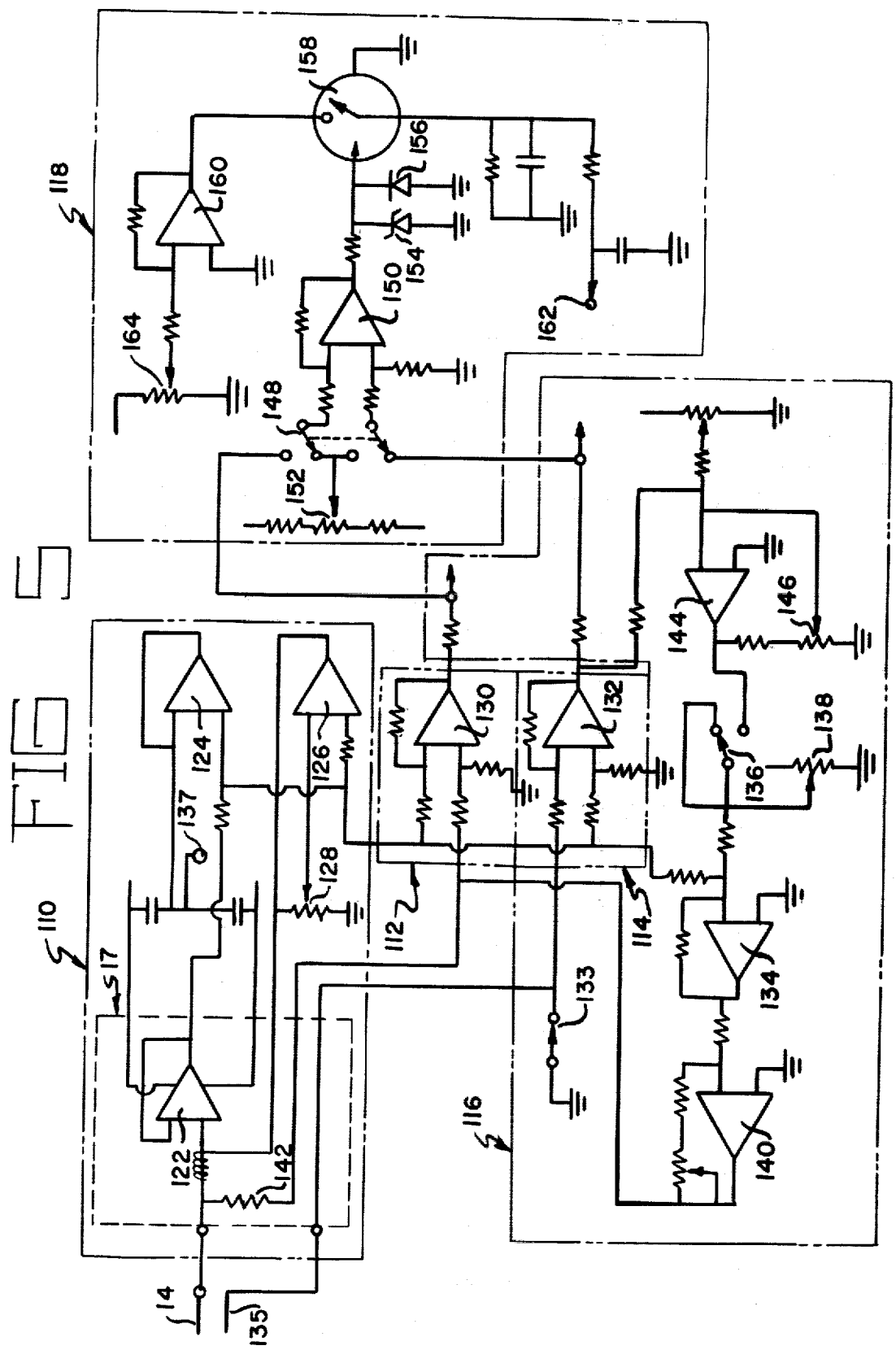

APPARATUS FOR MEASURING THE LOCAL VOID FRACTION IN A FLOWING LIQUID CONTAINING A GAS

CONTRACTUAL ORIGIN OF THE INVENTION

The invention described herein was made in the course of, or under, a contract with the UNITED STATES DEPARTMENT OF ENERGY.

BACKGROUND OF THE INVENTION

This invention relates to the measurement of the void fraction in two-phase flows.

The void fraction in a material is defined as the ratio of the volume of gas to a total volume under consideration that includes the gas. The term "void fraction" has also been applied to give a measure of the amount of gas present in a mixture of a gas and particulate matter such as is found in a fluidized bed. That use will be excluded from our description of the term since the consideration here is limited to the void fraction in a flowing liquid containing a gas. The word "local" is also used to refer to measurements that are made in a region that approximates a point in contrast to the term "global" which provides a measure of the average ratio of gas to liquid. It can be expected that local measurements of the void fraction in a mixture of a liquid and a gas will provide information about the sizes of voids and their spatial distribution in the fluid. Two-phase flows of the type described here are commonly encountered in applications involving liquid-metal magnetohydrodynamics and also in experiments connected with development of liquid-metal fast-breeder reactors. Some of the combinations of liquids and gases that have been used in two-phase systems are mixtures of NaK and nitrogen, liquid tin and steam, and air and water.

Many methods have been used in the past to measure void fraction. A summary of the present state of the art is given in a report entitled "Experimental Methods in Two-Phase Flow Studies," prepared for the Electric Power Research Institute and published in EPRI NP-118, dated March 1976. Methods in use include a measurement of the attenuation of a beam of X-rays or gamma rays that is passed through the flowing stream. It is often useful to measure the flux of gamma rays with the flow conduit full of the gas and then measure with the conduit full of the liquid to establish the extremes of attenuation and to derive or infer a relationship to associate particle density in the beam with the global void fraction. Another method of determining void fraction is to calculate it from the measurement of a pressure drop between two locations in the stream. This also is a global method. A third method, the hot-film probe, makes use of the fact that the heat transfer from a hot-film probe into a flowing liquid stream is different when the liquid contains bubbles. The hot-film probe makes local measurements. Another local method is the optical probe which passes light down a probe to its tip which is exposed to the fluid stream. Some light is reflected back from the tip. The presence of a gas void at the tip of the optical probe varies the index of refraction at the tip and hence affects the light that is reflected back from the probe. Other methods of measuring the void fraction include the use of quick-closing valves to trap a sample in a flow channel and determine how much of the trapped sample is liquid and how much is gas. This method and most of the photographic methods that make use of changes in density or other properties of the fluid are also global methods. Of the local methods, the hot-film probe requires more costly and complicated instrumentation and is affected by changes in the temperature of the fluids in which the void fraction is to be measured. The optical probe can only be used in a limited number of fluid-gas combinations.

An impedance-variation probe has been used with success to measure the local void fraction in various two-component streams at low velocities. The impedance-variation probe connects electrically to the fluid stream and uses the variation in impedance between the probe tip and a fluid ground to detect the presence of a gas void or a continuum of liquid at the tip. When bubbles contact the impedance-variation probe, the current flow is affected by the change in impedance or resistance that is represented by the bubble. With impedance-variation probes now in use, the conducting tip is of the order of 0.025 to 0.25 mm. The use of such probes has been hampered in the past by the fact that the combination of distributed capacitance of the probe and the desirability of having a small conducting probe area to approximate point measurements leads to a relatively long time constant. It is evident that, if the combination of void size and stream velocity is such that the time necessary for a complete void to pass the tip of a probe is not considerably greater than the RC product of the tip, then the probe will require special treatment to resolve two adjacent voids, or even to detect a small, fast-moving void at all.

It is an object of the present invention to provide a better apparatus for measuring the void fraction in a fluid stream made up of a liquid and a gas.

It is a further object of the present invention to provide an apparatus including an impedance-variation probe and an electronic circuit to resolve and identify small voids in a fluid stream including a liquid and gas-filled voids.

Other objects will become apparent in the course of a detailed description of the invention.

SUMMARY OF THE INVENTION

The void fraction in a flowing liquid containing bubbles of gas is measured by placing an impedance-variation probe in the flowing liquid and applying a damped voltage or current across or through the probe. A feedback amplifier connected to the probe minimizes the effect of probe capacitance in detecting probe current or voltage and permits the resolution of signals from small bubbles. A digitizer in the circuit provides a clean signal that shows bubble sizes and frequencies at the tip of the probe when plotted as a function of time and shows void fraction when integrated with respect to time. Three embodiments of the probe are adapted to different conditions of measurement.

BRIEF DESCRIPTION OF THE DRAWINGS

FIG. 2 is a sectional side view of an impedance-variation probe for the practice of the present invention.

FIG. 3 is a sectional view of an alternate embodiment of an impedance-variation probe.

FIG. 4 is a sectional side view of a microcapillary impedance-variation probe for the practice of the present invention.

FIG. 5 is a circuit diagram of the electronic circuit of FIG. 1.

DETAILED DESCRIPTION OF THE INVENTION

Figure 1:
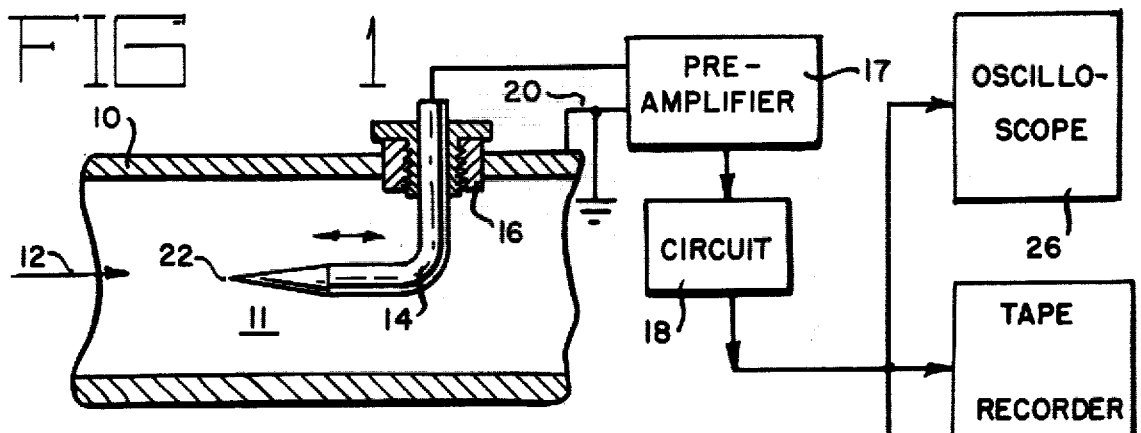
FIG. 1 is an overall block diagram of an apparatus for the practice of the present invention.

FIG. 1 is an overall sectional view and block diagram showing an apparatus for the practice of the present invention. In FIG. 1 a pipe 10 carries a fluid 11 flowing in a direction 12. It is of interest to measure the void fraction of the fluid 11 in pipe 10 when the flow comprises bubbles of gas in a liquid. To make this and other pertinent measurements, a probe 14 is placed inside pipe 10 and is brought through a coupling 16 to make an external connection to a preamplifier 17 that is part of an electronic circuit 18. An electric circuit is completed from the fluid 11 through probe 14, electronic circuit 18 and back through ground connection 20 to pipe 10, which is in contact with fluid 11. Probe 14 is adapted to detect changes in impedance at its tip 22 by applying one controlled electrical parameter to the probe and measuring another parameter. Probe 14 is also so disposed as to be movable within pipe 10 as indicated by the arrows in FIG. 1.

Various instruments are connected to the output of electronic circuit 18 to indicate the results of different measurements. Typically, a d-c voltmeter 24 is connected to the output of electronic circuit 18 to provide an averaged measurement of the voltage at probe 14. This voltage can be set to correspond to the void fraction in fluid 11. It is also convenient to obtain a plot of probe voltage as a function of time on oscilloscope 26. When the proper time scales are chosen as a function of fluid velocity and bubble size, it is possible to obtain an oscilloscope display that gives a measure of bubble size. For this purpose, it is most convenient to use a storage oscilloscope for oscilloscope 26 and to make single traces for observation. For a detailed measure of bubble sizes, it is also convenient to store information representing the probe voltage as a function of time on a tape recorder 28. Details of the information obtained on voltmeter 24, oscilloscope 26 and tape recorder 28 will be discussed below.

FIGS. 2, 3 and 4 are three alternate embodiments of probe 14 of FIG. 1. FIG. 2 is a ruggedized version of a probe that is adapted to detect larger gas voids than the probes 14 of FIGS. 3 and 4. In FIG. 2, a wire 30 having a diameter of the order of 0.032 inches is bent to form a tip 32 that is machined to a fine point. Wire 30 is connected by soldering or similar means at an end opposite to the tip 32 to hookup wire 34 which is then brought out for external connections. The connection 36 between wire 30 and hookup wire 34 is covered with an insulating sleeve 38. It is often convenient to make wire 30 of a nickel-chromium alloy such as Nichrome and to use a shrink tubing for sleeve 38. Wire 30 is insulated electrically everywhere except at tip 32, first by an applied coating 40 of epoxy resin, then by tubing 42 which is of stainless steel or the like. A collar 44 has external threads 46 for connection into a pipe and has an O-ring 48 which maintains a seal with cap 50. Probe 14 may be moved longitudinally in collar 44 to place tip 32 at different locations in a fluid stream or it may be locked in a desired position by tightening set screw 52.

The materials described above for components of probe 14 may vary depending upon the nature of the fluids to be measured. For example, if the fluid is at a high temperature, it may be desirable to make coating 40 of glass that is connected to tubing 42. In such a case, the easiest way to make the tip 32 is to place a wire 30 in a hollow glass tube that is then heated and drawn to a point.

FIG. 3 is an alternate embodiment of a probe 14. In FIG. 3, tip 32 is a short piece of platinum wire having a diameter of the order of 1 mil (approximately 0.025 mm.). The platinum wire is concentric with and is insulated from an electrically conducting needle having an outside diameter of the order of 12 mils (approximately 0.30 mm.). The combination of needle 56 and platinum wire 54 is of the kind that is available commercially as a Polarographic Sensor, a trademark of A-M Systems, Inc. The needle 56 is connected to a shielded cable 58, the shield of which is connected to electrically conducting tubing 60 which is typically made of stainless steel or the like. A collar 44 like that of FIG. 2 serves to place the probe 14 of FIG. 3 in a pipe for measurement and to permit motion of the probe 14 while maintaining a seal. The cable 58 of FIG. 3 is shown here as terminating in a BNC connector 62. This is a matter of choice at a convenience of the operator of the equipment. The probe 14 of FIG. 3 is adaptable for making measurements that distinguish bubbles that are extremely small, smaller than those that can be resolved by the probe 14 of FIG. 2.

A second alternate embodiment of the probe 14 is shown in FIG. 4 which is a microcapillary glass probe. In FIG. 4, a glass capillary tube 64 is connected through an end cap 66 to a reservoir 68. End cap 66 and reservoir 68 are typically made of an acrylate polymer. Reservoir 68 is filled with an electrolyte such as 2 M KCl or the like which makes electrical contact with a fluid stream through capillary tube 64. A pellet 70 of silver chloride or the like is pressed into the reservoir 68 and is connected to a plug 72 that permits removal of the structure just described from socket 74. Support for the components is supplied by cylindrical metal tubing 76 which is connected at a right angle to cylindrical metal tube 78 and then to tube 80. Electrical shielding is provided by using shielded coaxial cable. A collar 44 like those described for FIGS. 2 and 3 provides support at a pipe wall and an O-ring seal while permitting sliding motion of tube 80 to locate probe 14 of FIG. 4 at a desired point for measurement. The probe 14 of FIG. 4 is adapted particularly well for making measurements of small voids in a mixture of air and water.

It has been stated that the probes of FIGS. 2, 3 and 4 are used to make contact with a fluid containing both a liquid and a gas so that when the point of contact of the probe is in the liquid an electric circuit is completed with one value of impedance and when the gas is in electrical contact with the probe a different value of impedance, much higher, is introduced into the electric circuit. It is evident by inspection that one factor determining the size of bubbles that can be resolved is the area of the probe that is in electrical contact with the bubbles. If the probe area is larger than a bubble that strikes the probe, then there will be little or no indication of a change in impedance. It follows that one way of increasing the resolving ability of the probe is by reducing the area of the probe that is in electrical contact with the fluid. However, as this generates an ability to resolve smaller bubbles, it produces a corresponding disadvantage in that the time constant of the measurement may mask the detection of bubbles. The electronic circuit that is connected to any one of the probes of FIGS. 2, 3 or 4 must exhibit in combination with the probe a time constant that permits resolution of bubbles to a desired size. This objective is achieved with the probe circuit of FIG. 5. In FIG. 5, a high-input-impedance amplifier 110 is connected to a probe 14. An output signal from feedback amplifier 110 is taken to a current output amplifier 112 and a voltage output amplifier 114. One or the other of these outputs is used depending on whether the circuit of FIG. 5 is operated as a current clamp, measuring probe voltage, or as a voltage clamp, measuring probe current. Either of these modes of operation is possible and can be selected by setting switches as shown later. The probe is driven by a signal from the unity-gain feedback amplifier 116, and the output of either current output amplifier 112 or voltage output amplifier 114 is selected and processed in digitizer 118. The output of digitizer 118 provides a measure of the size and frequency of bubbles when displayed or detected as a time-varying signal and it provides a measure of the void fraction in the fluid when the output signal is integrated over a relatively long period of time.

The circuit of FIG. 5 includes an electrically shielded preamplifier 17 that is placed near the probe 14. Preamplifier 17 comprises an operational amplifier 122 of unity gain that is connected in a feedback mode. An output of operational amplifier 122 is connected to operational amplifier 124 which is connected back to operational amplifier 122 in a configuration that provides a high input impedance for preamplifier 17. The output of operational amplifier 124 is connected to floating common point 137, which is typically connected to an electrical shield about preamplifier 17 and to the shield of coaxial cable connected to probe 14. The output of operational amplifier 122 is also taken as an input to operational amplifier 126, the output of which is coupled capacitively to the input of operational amplifier 122 to provide feedback that is adjustable in an amount selected by potentiometer 128. The setting of potentiometer 128 is selected to minimize the effect of the input capacitance of the probe.

The output signal from preamplifier 17 is also coupled as an input to operational amplifiers 130 and 132. Operational amplifier 130 is connected in a feedback configuration to comprise current output amplifier 112, and operational amplifier 132 is connected in a feedback configuration to comprise voltage output amplifier 114. With switch 133 in the position shown, the local fluid ground is connected to the circuit electrical ground through grounding pin 135. With switch 133 open, one of the inputs to operational amplifier 132 floats with respect to the local fluid ground. The output of preamplifier 17 is also taken as an input to operational amplifier 134 where it is added to a signal that is coupled through switch 136. With switch 136 in the position shown, the value of voltage selected from potentiometer 138 is added as an input to operational amplifier 134. This value is the current set that is used when it is desired to drive probe 14 at a constant current and monitor the voltage across probe 14. The value selected by switch 136 is amplified further in operational amplifier 140 and is applied through a precision resistor 142 to probe 14. When it is desired to clamp the voltage on the probe and measure current, then the switch 136 is placed in the opposite position which connects an output signal from voltage amplifier 114 to operational amplifier 144. Variable resistor 146 sets the gain of operational amplifier 144 and the voltage signal at the output of operational amplifier 144 is then coupled through switch 136 through the feedback loop of operational amplifiers 134 and 140 to probe 14 to clamp the voltage.

As stated, switch 136 is presently in the position in which probe current is clamped and probe voltage is measured. Switch 148, a double-pole, double-throw switch, is set in conjunction with switch 136 so that switch 148 selects the output of current output amplifier 112 to be amplified in operational amplifier 150. Operational amplifier 150 is also connected through switch 148 to a potentiometer 152 to connect a proper offset voltage to the desired terminal of operational amplifier 150. The output of operational amplifier 150 shunted by zener diode 154 and diode 156 is connected as an input to digital switch 158 which controls an internal field-effect transistor to switch the voltage output of operational amplifier 160 either on or off at output terminal 162. Potentiometer 164 is adjustable to select a desired value of voltage to be switched to terminal 162 when digital switch 158 is caused to conduct. If potentiometer 164 is set to produce an output of 1 volt from operational amplifier 160, then a voltmeter connected at terminal 162 with a time constant that is long compared to the period of passage of bubbles will read the void fraction directly.

The effect of potentiometer 152 together with zener diode 154 and diode 156 is to allow the operator to select a minimum level of pulse that will cause operation of digital switch 158, comprising a digitizer. This is effective to prevent electrical noise from triggering digital switch 158 and also permits discrimination against bubbles that are too small to let the circuit reach its full value of voltage or current during the time it takes the bubble to pass probe 14. The output at terminal 162 is thus seen to be a square wave that is a "clean" version of the output of voltage amplifier 114 or current amplifier 112, whichever is selected by switch 158.

The circuit of FIG. 5 has been built and used at the Argonne National Laboratory. Major components used in the circuit that was built are listed in the table that follows.

TABLE

| Reference numbers | Component | Manufacturer or ID |
|---|---|---|
| 122 | Amplifier | National Semiconductor LH0022 |
| 124, 126, 134, 140, 144, 150, 160 | Amplifier | Signetics 536 |
| 130, 132 | Amplifier | Precision Monolithics OP-05 |
| 158 | Digital Switch | Signetics DG-200BA |
| 154 | Zener diode | 1N736(3.3 v.) |
| 156 | Diode | 1N444B |

Figure 6:
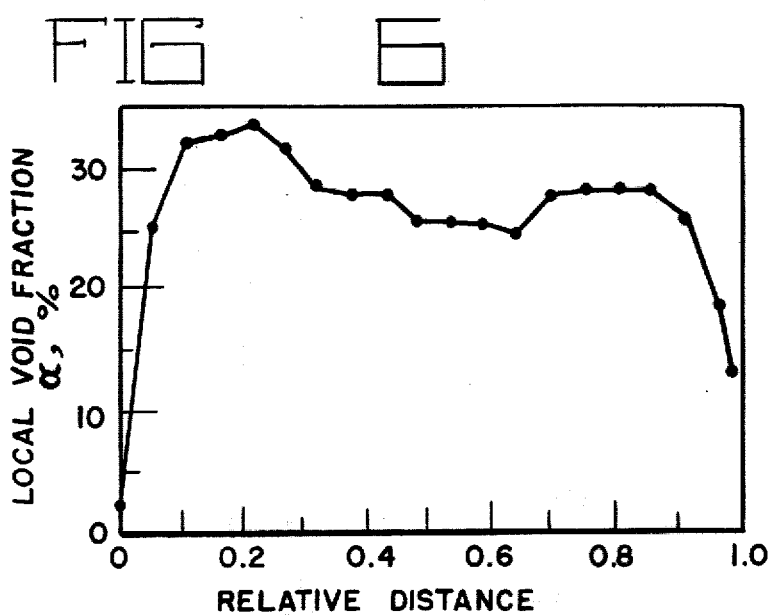
FIG. 6 is a plot of the local void fraction as a function of the relative distance across a channel as obtained by the apparatus of the present invention.
Figure 7:
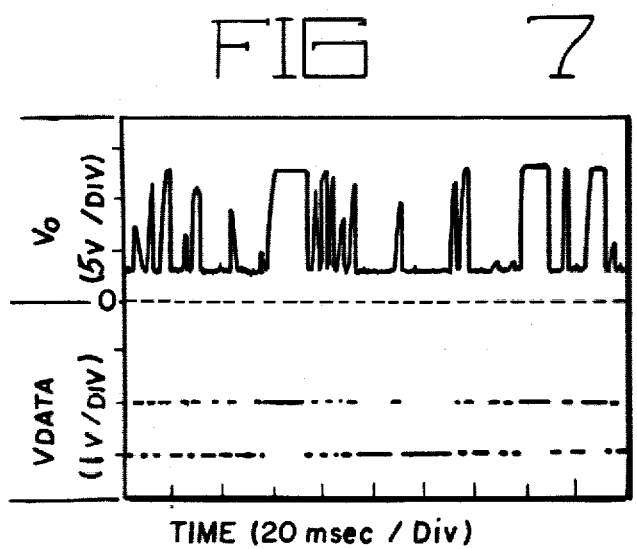
FIG. 7 is a copy of an oscilloscope trace showing various voltage outputs of the circuit of FIG. 5.

Experimental results of the use of the apparatus of the present invention are shown in FIGS. 6 and 7. FIG. 6 is a plot of the local void fraction as a function of distance across a channel, normalized to unity. In FIG. 6, a probe like that of FIG. 2 was moved in increments equal to approximately 5% of the distance across the channel carrying a mixture of air and water. The probe was connected in the current-clamp mode in a circuit like that of FIG. 5 and the output of terminal 162 of the circuit was applied to a voltmeter having a time constant that was long compared to the time necessary for a bubble to pass. The local void fractions are seen to vary from approximately 2% near one wall to as high as 33% and the average value of the points indicated in FIG. 6 was determined to be 26.9%. This compared favorably (well within experimental error) with a figure of 28.0% that was obtained by using the well-known gamma-ray attenuation method on the same fluid stream. A portion of the data obtained from a comparable measurement is shown in FIG. 7 which is a time plot of oscilloscope traces of two voltages obtained as a function of time. The upper trace in FIG. 7 is a plot of the output of voltage output amplifier 114 of FIG. 5 as obtained in the current-clamp mode. The lower trace is the output of terminal 162 of FIG. 5 at the same time. The lower trace is seen to be clean and noise-free and it appears by inspection that the signals in the upper trace of FIG. 7 that indicate bubbles that are less than the time constant of the circuit have been converted in the lower trace into square waves of the width of the short pulses in the upper trace. When the data of FIG. 7 were obtained, the threshold was set to discriminate against noise but to pass the signals resulting from small bubbles. It would be possible to eliminate the shorter spikes in the upper trace of FIG. 7 by varying the setting of potentiometer 152 of FIG. 5. The traces that are shown in FIG. 7 for a brief period of time could be displayed over longer intervals by making a tape recording that corresponds to the output voltage and printing the taped record to show a scaled measure of the sizes of bubbles at the tip of the probe.

The embodiments of the invention in which an exclusive property or privilege is claimed are defined as follows:

1. An apparatus for measuring a local void fraction in an electrically-conducting flowing liquid containing a gas, the apparatus comprising:
   an impedance-variation probe having a conducting tip disposed in the flowing liquid;
   means connected electrically to the probe and the flowing liquid for applying a controlled first electrical parameter to the probe;
   probe energization means disposed within said probe including an electrically conductive shield and circuit means for applying a first electrical parameter to the probe, and for applying an electrical signal to said shield;
   a feedback amplifier connected electrically to the probe and the flowing liquid to respond to a second electrical parameter, said feedback amplifier providing an output signal comprising a first series of signals corresponding to the presence of the fluid at said conducting tip of said probe and a second series of signals interspersed with said first series of signals, corresponding to the presence of voids at said conducting tip of said probe, said output signal maintaining the relative time duration of each signal of said first and second series of signals; and
   integrating means connected to said feedback amplifier to generate therefrom a time integral of the output signal of said feedback amplifier, which time integral is proportional to the local void fraction in the flowing liquid.

2. The apparatus of claim 1, wherein said electrical signal applied to said shield maintains said shield at substantially the voltage level of said conducting tip of said probe.

3. The apparatus of claim 2 wherein the first controlled electrical parameter is voltage and the second electrical parameter is current.

4. The apparatus of claim 2 wherein the first controlled electrical parameter is current and the second electrical parameter is voltage.

5. The apparatus of claim 2 wherein the integrating means comprise a voltmeter having a time constant that is long in comparison with a time for passage of gas voids.

6. The apparatus of claim 5 comprising in addition means connected to the amplifying means for recording an output voltage of the amplifying means as a function of time, whereby a measure is provided of size and frequency of voids at the top of the probe.

7. The apparatus of claim 6 wherein the impedance-variation probe is movable within the flowing liquid.

8. The apparatus of claim 1, wherein said feedback amplifier further comprises circuit means to minimize the input capacitance of said probe.

9. The apparatus of claim 1, wherein said probe tip and said shield comprises a wire within a hollow needle.

10. The apparatus of claim 1, wherein said probe tip comprises a capillary tube containing an electrolyte solution.

* * * * *